United States Patent [19]

Bobee et al.

[11] Patent Number: 5,438,072
[45] Date of Patent: Aug. 1, 1995

[54] TAXOID-BASED COMPOSITIONS

[75] Inventors: Jean-Marc Bobee, Verrieres-le-Buisson; Patrick de Lanty, Paris; Gilles Guerin, Eaubonne; Michel Veillard, Sceaux, all of France

[73] Assignee: Rhone-Poulenc Rorer S.A., Antony Cedex, France

[21] Appl. No.: 155,543

[22] Filed: Nov. 22, 1993

[30] Foreign Application Priority Data

Dec. 2, 1992 [FR] France ............................... 92 14501

[51] Int. Cl.⁶ .............................................. A01N 43/02
[52] U.S. Cl. ................................................... 514/449
[58] Field of Search .......................... 514/449; 549/510

[56] References Cited

U.S. PATENT DOCUMENTS

| | | | |
|---|---|---|---|
| 4,507,217 | 3/1985 | Sears | 252/62.54 |
| 4,534,899 | 8/1985 | Sears | 260/403 |
| 4,814,470 | 3/1989 | Colin et al. | 514/449 |
| 4,960,790 | 10/1990 | Stella et al. | 514/449 |

FOREIGN PATENT DOCUMENTS

| | | |
|---|---|---|
| 0118316 | 9/1984 | European Pat. Off. . |
| 0253738 | 1/1988 | European Pat. Off. . |
| 0522937 | 1/1993 | European Pat. Off. . |
| WO93/00928 | 1/1993 | WIPO . |
| WO93/00929 | 1/1993 | WIPO . |

OTHER PUBLICATIONS

Chemical Abstracts, vol. 106, No. 22, abstract No. 182581c (1987).
Journal of the National Cancer Institute, vol. 82, No. 15, Aug. 1, 1990, pp. 1247–1259, "Taxol: A Novel Investigational Antimicrotubule" Agent, E. Rowinsky, et al.

*Primary Examiner*—Richard L. Raymond
*Assistant Examiner*—Deborah Lambkin
*Attorney, Agent, or Firm*—Morgan & Finnegan

[57] ABSTRACT

The present invention relates to new taxoid-based compositions consisting of solutions of these derivatives in a surface-active agent.

These solutions are used for preparing perfusion solutions.

8 Claims, No Drawings

TAXOID-BASED COMPOSITIONS

FIELD OF THE INVENTION

The present invention relates to a new pharmaceutical form based on a therapeutic agent having an antitumour and antileukaemic activity. It relates more particularly to a new injectable form containing taxoids such as taxol, taxotere or derivatives of the following general formula:

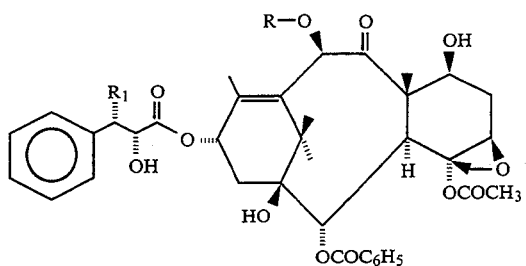

In Formula (I), R represents a hydrogen atom or an acetyl radical, the symbol $R_1$ represents a tert-butoxycarbonylamino or benzoylamino radical. Among these derivatives as a whole, the two derivatives for which R represents an acetyl group and $R_1$ a benzoylamino group or that for which R represents a hydrogen atom and $R_1$ a tert-butoxycarbonylamino radical, are preferred.

The first of these two compounds is more widely known by the name of taxol, the second is known by the name of Taxotere.

These products exhibit, in vivo, a substantial activity on malignant tumors which has made it possible to study them in the treatment of diseases which are resistant to all other anticancer therapies.

Unfortunately, these products exhibit a water-solubility which is so low that it has been necessary to prepare a formulation for injection based on a surface-active agent and ethanol. Ethanol is the best pharmaceutical solvent which makes it possible to solubilize molecules corresponding to formula (I).

By way of example, according to the publication by Rowinsky, Lorraine, Cazenave and Donehower which appeared in the Journal of the National Cancer Institute, vol. 82, No. 15, pages 1247 to 1259, on 1st Aug. 1990, a first solution, called "stock solution", containing about 6 mg/ml of taxol, is prepared in a solvent mixture composed of:

50% by volume of ethanol
50% by volume of Cremophor EL.

During the injection, this solution is mixed with a perfusion liquid containing sodium chloride or dextrose. In order to obtain a mixture which is stable from a physical point of view as well as from a chemical point of view, the authors of this article state that the concentration of active ingredient in the perfusion solution should be limited to concentrations of about 0.03 to 0.6 mg/ml (see preceding publication page 1251, column 1, third paragraph).

Now, it is desirable to be able to inject sufficient doses of active ingredient, for that, clinicians wish to inject active ingredient concentrations of between about 0.3 and 1 mg/ml in the perfusion liquid; above these doses, anaphylactic shock phenomena appear which are difficult to control, essentially due to the Cremophor (see the publication by Rowinsky, page 1250 second column, last paragraph).

Still according to this publication, in order to obtain such concentrations (between 0.3 and 1 mg/ml) it is necessary to inject solutions containing, at the same time as active ingredient, the following concentrations of each of the following compounds, ethanol and especially Cremophor, of about 8 g per 100 ml of perfusion solution. The treatment often requires the administration of high doses of active ingredient and the concentration of active ingredient in the solution being relatively low, the injection of a large volume has the effect of causing, during the treatment, in addition to the anaphylactic manifestations, manifestations of ethylism.

It has been discovered, according to the French Application filed under the number 91,08527, that the use of completely new pharmaceutical forms made it possible either to substantially reduce the concentrations of ethanol, or alternatively to completely remove the Crémophor and the ethanol from the perfusion solution.

For that, according to a first embodiment of this patent application, a stock solution containing the active ingredient was prepared in a mixture of solvents composed of ethanol which is the best solvent biocompatible with active ingredients of the class of taxanes and a surface-active agent chosen from the polysorbates marketed especially under the names Tween and Montanox, or the ethylene oxide ester-ethers and fatty acid glycerides (castor oil hydrogenated or otherwise) marketed for example under the name Cremophor or Emulphor.

The stock solution was prepared by dissolving the active ingredient in ethanol then gradually adding the surface-active agent. Solutions could thus be prepared containing 10 to 100 mg/ml of active ingredient in a mixture containing about 50% surface-active agent. The ethanol contained in this solution was then removed, at least partially, by evaporation under vacuum or by any other appropriate means.

According to a second process for preparing the stock solution, the active ingredient was directly dissolved in the surface-active agent. According to a better way of implementing the invention, a solution of surface-active agent containing especially 1 to 2% ethanol was prepared and the active ingredient was continuously added to this solution while stirring by means, for example, of a propeller mill or a disintegrating turbine. The presence of a small quantity of ethanol provides several advantages, the medium has a low viscosity, the wetting of the powder is enhanced as well as the final filtration of the solution.

The stock solution, with low ethanol content, preferably contains less than 5% ethanol, it also contains more preferably less than 2% ethanol. This solution is stable and may thus contain up to 200 mg/ml, and preferably up to 80 mg/ml of active ingredient in the surface-active agent.

The taxol stock solution had according to this invention a concentration of between 6 and 20 mg/ml of active ingredient in the surface-active agent. The Taxotère stock solution preferably had a concentration of between 20 and 80 mg/ml of active ingredient in a surface-active agent.

These solutions in the surface-active agent, optionally containing small quantities of ethanol, could be dissolved in the perfusion solution, but with an extremely vigorous stirring, for example by means of a Vortex type apparatus. Given that this type of equipment does not exist in all hospitals, it was necessary to facilitate the dissolution of the above composition and this is the object of the present invention.

Another solution for dissolving the stock solution in the perfusion solution consists in heating the mixture at around 40° C. But in this case, the compound of formula (I) is partially degraded.

The present invention therefore consists in producing an intermediate solution between the solution of the derivatives of the class of taxanes in the surface-active agent and an aqueous solution containing an additive which subsequently promotes the dissolution of the said intermediate solution in the perfusion solution.

These additives are chosen from the range of additives which are capable of breaking or avoiding the formation of the gelled phase which is formed between the emulsifier containing the derivative of the class of taxanes and the water.

Among the additives which make it possible to break or avoid the formation of this gelled phase, there may be mentioned the derivatives having a molecular weight equal to or less than about 200. Among these compounds, those carrying at least one hydroxyl functional group or one amine functional group, such as amino acids, are even more preferred.

There may be mentioned, by way of examples of such compounds:
ethanol
glucose
glycerol
propylene glycol
glycine
sorbitol
mannitol
benzyl alcohol
polyethylene glycols.

Inorganic salts such as sodium chloride may also be used.

The quantity of additive used varies as a function of the nature of the additive, it is preferably greater than 6% by weight relative to the mass of surface-active agent, and still more preferably greater than 15% by weight for polyols such as glycerol, glucose or sorbitol.

The solutions of taxoids in the surface-active agent with the aqueous solution of the dilution additive are preferably provided in ampoules, bottles or a double compartment device which allow the mixing, immediately before use, of the two solutions at the time of injecting into the perfusion bag.

The Taxotère or taxol perfusions are then injected into man at a predetermined rate as a function of the quantity of active ingredient which it is desired to inject. The anaphylatic shock phenomena which were observed with the prior art solutions are not observed with these solutions.

Thus, these last perfusions have made it possible to decrease by about 80%, compared with the prior art, the quantities of surface-active agent injected into man.

EXAMPLES

The invention will be more completely described by means of the following examples which should not be considered as limiting the invention.

EXAMPLE 1

Preparation of the taxoids solution according to Patent Application 91,08527.

32 g of Taxotère are dissolved in 340 ml of absolute ethanol and then 830 g of Polysorbate 80 are added. The ethanol is evaporated by means of a rotary evaporator at 30° C. at a pressure of 15 mm of mercury (2000 Pa) for 2 hours.

The solution obtained is stable, it contains 40 mg/ml of Taxotère.

1 ml of this solution is mixed with 3 ml of an aqueous solution containing by mass 70% of water and 30% of glycerol. After stirring manually, the dissolution is total. In the case where the water/glycerol mixture is replaced by water alone, the formation of a heterogeneous gel is observed after stirring. The same result is obtained, that is to say a fluid solution, by adding only 2 ml of the aqueous glycerol solution.

EXAMPLE 2

Example 1 is repeated, replacing the glycerol solution with an aqueous glucose solution containing 35% by weight of glucose. After stirring manually, the solution is fluid.

EXAMPLES 3 TO 4

Example 1 is reproduced, replacing the Polysorbate with various surface-active agents, the results are indicated in the table below:

| TEST | SURFACE-ACTIVE AGENT | Dilution mixture | Observation |
| --- | --- | --- | --- |
| 3 | Crémophor EL | Water-glycerol (64/36) | fluid |
| 4 | Crémophor RH 40 | Water-glycerol (64/36) | fluid |
| C1 | Crémophor EL | water | caking |
| C2 | Crémophor RH 40 | water | caking |

EXAMPLES 5 TO 12

The procedure is carried out under the same conditions as in Example 1, but mixing 1 g of Polysorbate 80 with 1 g of the dilution mixture indicated in the table below: the nature of the liquid phase obtained is observed.

| TESTS | DILUTION MIXTURE (% by mass) | PROPORTIONS additive(s)-Tween 80 (% by mass) | APPEARANCE OF THE MIXTURE |
| --- | --- | --- | --- |
| 5 | water: 62<br>glycerol: 38 | glycerol: 27.5<br>Tween 80: 72.5 | fluid |
| 6 | water: 62<br>sorbitol: 38 | sorbitol: 27.5<br>Tween 80: 72.5 | fluid |
| 7 | water: 62<br>PEG 200: 38 | PEG 200: 27.5<br>Tween 80: 72.5 | fluid |
| 8 | water: 62<br>glucose: 38 | glucose: 27.5<br>Tween 80: 72.5 | fluid |
| 9 | water: 62<br>propylene glycol: 38 | propylene glycol: 27.5<br>Tween 80: 72.5 | fluid |
| 10 | water: 78<br>NaCl: 22 | NaCl: 15.4<br>Tween 80: 84.6 | fluid |
| 11 | water: 62<br>glycerol: 19<br>glucose: 19 | glycerol: 13.8<br>glucose: 13.8<br>Tween 80: 72.4 | fluid |
| 12 | water: 62<br>glycerol: 15.2<br>glucose: 15.2<br>NaCl: 7.6 | glycerol: 11.0<br>glucose: 11.0<br>NaCl: 5.5<br>Tween 80: 72.5 | fluid |

EXAMPLES 13 TO 14

To a solution of 6 g of Polysorbate 80, are added x g of additive and 4 ml of water, the fluidity of the medium is observed.

The results are indicated in the table below:

| Test | Additive | Result |
|------|----------|--------|
| 13 | benzyl alcohol 0.5 g | fluid |
| 14 | glycine 0.4 g | fluid |
| 15 | glycol 1.90 g | fluid |
| 16 | ethanol 0.60 g | fluid |
| 17 | glycerol 0.53 g<br>ethanol 0.53 g | fluid |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Injectable compositions useful for the preparation of perfusion solutions comprising taxane derivatives, wherein formation of a gelled phase during mixing of the compositions with an aqueous solution is avoided or wherein any gelled phase formed during mixing of the composition with an aqueous solution can be broken, said composition comprising a solution convenient for storage of said taxane derivatives in a surface active agent selected from polysorbates, ethylene oxide esters-ethers and fatty acids glycerides, and a water solution of an effective amount of a dilution additive selected from organic compounds having a hydroxyl group an amine functional group and a molecular weight of less than 200 or sodium chloride.

2. Injectable compositions according to claim 1, wherein the dilution additive is an amino acid.

3. Compositions according to claim 1, wherein the weight ratio between the additive and the surface-active agent is greater than 6%.

4. Compositions according to claim 1, wherein the weight ratio between the additive and the surface-agent is greater than 15%.

5. Compositions according to claim 1, wherein the additive is selected from glucose, glycerol, sorbitol, mannitol, glycine, polyethylene glycols, propylene glycol, benzyl alcohol and ethanol.

6. Compositions according to claim 1, wherein the derivative of the class of taxanes is selected from the derivatives of formula (I)

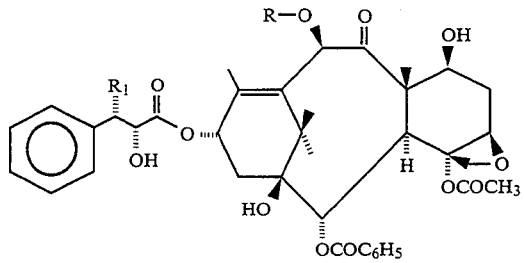

in which R represents a hydrogen atom or an acetyl radical, the symbol $R_1$ represents a terbutoxycarbonylamino or benzoylamino radical.

7. Compositions according to claim 6, wherein in the compound of formula (I) R represents an acetyl group and $R_1$ represents a benzoylamino radical.

8. Compositions according to claim 6, wherein in the compound of formula (I) R represents hydrogen and $R_1$ a tert-butoxycarbonylamino radical.

* * * * *

UNITED STATES PATENT AND TRADEMARK OFFICE
CERTIFICATE OF CORRECTION

PATENT NO. : 5,438,072
DATED : August 1, 1995
INVENTOR(S) : BOBEE et al.

It is certified that error appears in the above-indentified patent and that said Letters Patent is hereby corrected as shown below:

Column 2, line 28, delete "ethylene oxide ester-ethers" and insert therefor --ester-ethers of ethylene oxide.--

In the Claims, claim 1, line 36, delete "ethylene oxide esters-" and insert therefor --ester---.

line 37, after "ethers" insert --of ethylene oxide--; and line 37, delete "fatty acids" and insert therefor --of fatty acid--.

Signed and Sealed this

Eighth Day of April, 1997

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,438,072
DATED : August 1, 1995
INVENTOR(S) : Jean-Marc Bobee et al.

It is certified that error appears in the above-identified patent and that said Letters Patent is hereby corrected as shown below:

Column 5,
Line 39, change "hydroxyl group an amine" to -- hydroxyl group or an amine --.

Signed and Sealed this

Second Day of May, 2006

JON W. DUDAS
*Director of the United States Patent and Trademark Office*